United States Patent [19]

Hofmeister et al.

[11] Patent Number: 4,956,482
[45] Date of Patent: Sep. 11, 1990

[54] PROCESS FOR THE PREPARATION OF PREGNANE DERIVATIVES

[75] Inventors: Helmut Hofmeister, Berlin; Klaus Annen, Muenster-Albachten; Henry Laurent; Rudolf Wiechert, both of Berlin, all of Fed. Rep. of Germany

[73] Assignee: Schering Aktiengesellschaft, Berlin and Bergkamen, Fed. Rep. of Germany

[21] Appl. No.: 325,585

[22] Filed: Mar. 20, 1989

Related U.S. Application Data

[60] Continuation of Ser. No. 95,090, Sep. 11, 1987, which is a division of Ser. No. 776,923, Sep. 17, 1985, Pat. No. 4,708,823.

[30] Foreign Application Priority Data

Sep. 17, 1984 [DE] Fed. Rep. of Germany ....... 3434448

[51] Int. Cl.$^5$ ............................................... C07J 1/00
[52] U.S. Cl. .................................... 552/594; 552/595; 552/597; 552/598
[58] Field of Search ...................... 260/397.4; 568/346, 568/372

[56] References Cited

U.S. PATENT DOCUMENTS

4,102,908  7/1987  Hofmeister et al. .............. 260/397.4
4,567,002  1/1986  Hofmeister et al. ........... 260/397.45

OTHER PUBLICATIONS

Hofmeister et al., (1978) "Conversion of 17-α-Ethynyl Steroids", Chem. Ber. (111):3086–3093.

Primary Examiner—H. M. Sneed
Assistant Examiner—J. Saba
Attorney, Agent, or Firm—Millen, White & Zelano

[57] ABSTRACT

Known pregnane derivatives are prepared by esterification of know androstane derivatives to give new esters of Formula III

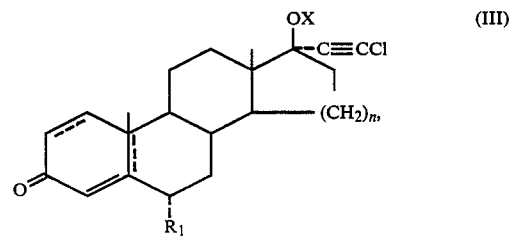

wherein
⋯ in each case symbolizes a single bond or a double bond,
n is 1 or 2,
$R_1$ is hydrogen or methyl,
$R_2$ is hydrogen or formyl, and
$R_3$ is chlorine, hydroxy or an alkanoyloxy group of up to 6 carbon atoms,
and reaction of the latter with Ag(I) and formic acid.

10 Claims, No Drawings

PROCESS FOR THE PREPARATION OF PREGNANE DERIVATIVES

This is a continuation of application Ser. No. 07/095,090 filed Sept. 11, 1987, which is a division of 06/776,923 filed Sept. 17, 1985, now U.S. Pat. No. 4,708,823, issued Nov. 23, 1987.

BACKGROUND OF THE INVENTION

The invention relates to a method for preparing pregnane derivatives and to certain intermediate esters useful therein.

For about ten years, 4-androstene-3,17-dione and 1,4-androstadiene-3,17-dione, produced by microbiological side chain degradation of sterols, have increasingly been utilized commercially as starting materials for the partial synthesis of pharmacologically effective steroids. As a consequence, the side chain buildup of androstane derivatives to form pregnane derivatives, which had even prior to this time been the object of intensive research activity (see, for example, J. Fried and J. A. Edwards: Organic Reactions in Steroid Chemistry, van Nostrand Reinhold Comp., New York, II: 127–236 [1976]), has increasingly gained in importance. Thus, 17α-ethynyl-17β-nitrooxy steroids (prepared by ethynylation of 17-oxo steroids and esterification of the resultant 17α-ethynyl-17β-hydroxy steroids with nitric acid in acetic anhydride) have been successfully converted into 17β-acetyl-17α-formyl steroids (Chem. Ber. 111: 3086–3096 [1978]). These compounds are convertible, by means of known methods, into pregnane derivatives of general Formula I below, the further conversion of which into pharmacologically active steroids is well known. For example all of the compounds of Formula I can be converted using conventional methods into pharmacologically active steroids, for example, hydrocortisone, cortisone, 6α-methylhydrocortisone, prednisolone, 6α-methylprednisolone, D-homoprednisolone, 9-chloroprednisolone, esters of these compounds, etc. For example, the 9,11-saturated compounds can be 11β-hydroxylated using microorganisms such as *Curvularia lunata*, etc. (See, e.g., W. Charney, H. L. Herzog, *Microbial Transformations of Steroids*, Academic Press, New York, etc., 1967); or to the 9,11-unsaturated compounds, HO-Cl or HO-Br can be added and, optionally, bromine cleaved. (See, e.g., GB No. 1,594,852; GB No. 2,089,809; GB No. 2,105,339; and U.S. patent applications Ser. No. 554,418 filed on Nov. 22, 1983; and Ser. No. 711,138 on Mar. 13, 1985.)

SUMMARY OF THE INVENTION

It is an object of this invention to provide a method for synthesizing these pregnane derivatives of general Formula I by a substantially simpler method than heretofore possible by means of conventional syntheses.

Upon further study of the specification and appended claims, further objects and advantages of this invention will become apparent to those skilled in the art.

These objects have been achieved by providing a process for the preparation of pregnane derivatives of Formula I

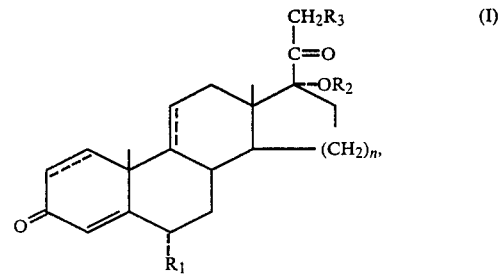

wherein

⋯ in each case symbolizes a single bond or a double bond, n is the number 1 or 2, $R_1$ is hydrogen or methyl, $R_2$ is hydrogen or formyl, and $R_3$ is chlorine, hydroxy or alkanoyloxy of up to 6 atoms, comprising esterifying an androstane derivative of Formula II

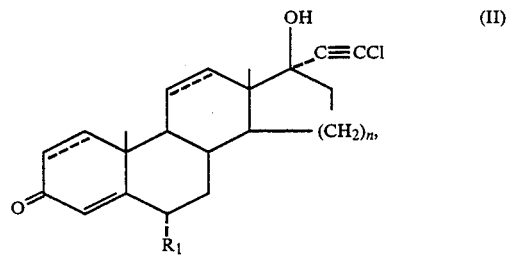

wherein ⋯ n and $R_1$ have the meanings given above, by means of nitric acid, trifluoroacetic acid or trichloroacetic acid, reacting the resultant esters of Formula III

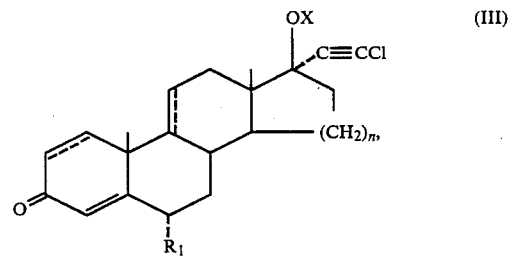

wherein

⋯ n and $R_1$ have the meanings give above and

X is a nitro group, a trifluoroacetyl group, or a trichloroacetyl group, in the presence of silver (I) salts, by means of formic acid to form pregnane derivatives of Formula Ia

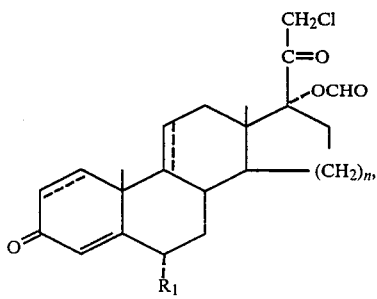

(Ia)

wherein ---- n and R₁ have the meanings given above, and, optionally, saponifying the thus-produced 17-formyl esters and/or exchanging the 21-chlorine atom against an alkanoyloxy group, and optionally, saponifying the latter.

These objects have also been achieved by providing the esters of Formula III

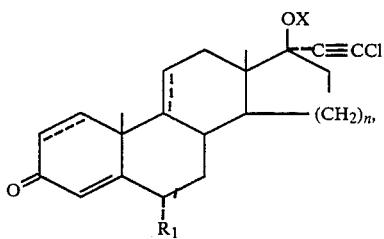

(III)

wherein
---- in each case symbolizes a single bond or a double bond,
n is the number 1 or 2
R₁ is hydrogen or methyl, and
X is nitro, trifluoroacetyl, or trichloroacetyl.

DETAILED DISCUSSION

The first stage of the process of this invention can be conducted under the conditions usually employed for the esterification of tertiary or sterically hindered steroid alcohols with nitric acid, trifluoroacetic acid or trichloroacetic acid. Esterification with trifluoroacetic acid or trichloroacetic acid can be accomplished, for example, under completely conventional conditions with the corresponding trihaloacetyl chlorides or hexahaloacetic anhydrides in the presence of bases, such as, for example, pyridine. Esterification with acetyl nitrate (Tetrahedron 25 761–769 [1969], modified according to Chem. Ber. 111: 3086–3096 [1978]) has proved to be especially suitable for supplying the nitric acid. The mixture required for this purpose can be prepared, for example, from the components (J. Amer. Chem. Soc. 82: 3588–3598 [1960]). Suitable also is nitric acid containing about 70–100% by weight of acid. The reaction is customarily performed at a reaction temperature of −50° C. to 0° C., preferably −30° C. to 10° C. The reaction time is normally 10–120 minutes. From a stoichiometric amount to an excess of acid component is usually employed, conventionally.

Basically, the second reaction step can be conducted under the conditions described in the above-cited publications, or variations thereof, e.g., as indicated in U.S. Pat. No. 4,102,908. These process conditions are not especially suited for industrial procedures, since the required processing of the wastes, which contain mercury (II) salts, is rather expensive. It is substantially simpler to conduct this reaction step with the use of silver(I) salts as the catalyst. The fact that the reaction step proceeds, under these conditions, in the desired way is surprising in dual respects. Based on the statements in the publication in Chem. Ber., it would have be expected, on the one hand, that no hydration of the ethynyl group would occur with silver(I) salts. On the other hand, it would also be expected that the chlorine atom of the starting compound or the final product may split off and render the silver catalyst ineffective by formation of silver chloride. Surprisingly, neither possibility occurs to the extent which could be expected.

Suitable catalysts employed for this process step include, preferably readily dissociating silver(I) salts, such as, for example, silver(I) nitrate, silver(I) acetate, silver(I) fluoride, or silver (I) sulfate. They are utilized preferably in a concentration of 0.01–0.5 mol-%, based on the steroid. In essence, any salt which provides the silver(I) cation is employable as longer as it is reaction compatible. This reaction step is conducted with preference in concentrated formic acid with a content of 95%–100% by weight of acid. Since formic acid serves as solvent, it is usually used in an amount of 5 to 50 times that of the steroid.

Just as in the reaction of steroids with an unsubstituted 17α-ethynyl side chain (Chem. Ber. 111: 3086–3096 [1978]), this reaction step will take place more uniformly by additionally admixing to the reaction mixture a dipolar aprotic or alkaline solvent. Suitable additives include, for example, tertiary amines, e.g. triethylamine or N-methylmorpholine, or amide-group-containing, dipolar aprotic solvents, such as dimethylformamide, N-methylacetamide, or also especially hexamethylphosphoric triamide or 1-methyl-2-pyrrolidone. Satisfactory results are achieved, in general, by adding to the reaction mixture 10–50% of this solvent, based on the remaining components. This stage of the reaction is usually performed at a temperature of 0° –150° C. and times of 2–16 hours when conducted at room temperature.

The optionally following saponification of the 17-formyl esters takes place under the conditions sufficiently known to those skilled in the art. For example, these compounds can suitably be saponified in an optionally aqueous, lower alcohol (methanol, ethanol, propanol or isopropanol) in the presence of alkaline catalysts (for example the corresponding sodium alcoholate or potassium alcoholate, sodium hydroxide, potassium hydroxide, sodium carbonate, potassium carbonate or potassium bicarbonate). Normally, a temperature of between 0° C. and the boiling point of the solvent is chosen as the reaction temperature.

The optionally subsequently conducted exchange of the 21-chlorine atom against an alkanoyloxy group likewise takes place under conventional conditions; thus, for example, by reacting the compounds in an inert solvent with the corresponding sodium or potassium alkanoate. Suitable solvents include, for example, lower ketones, such as acetone, methyl ethyl ketone, or methyl isobutyl ketone, or dipolar aprotic solvents, such as dimethylformamide, N-methylacetamide, dimethyl sulfoxide, 1-methyl-2-pyrrolidone or hexamethylphosphoric triamide. The reaction is usually conducted at a temperature of 50–120° C.

The optionally subsequently performed saponification of the 21-alkanoyloxy compounds can be effected under the same conditions as the saponification of the 17-formyl compounds.

The starting compounds for the process of this invention are known and can be synthesized, for example, according to conventional methods (Chem. Soc., 1962: 4995).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) At $-20°$ C., 6.5 ml of fuming nitric acid is added dropwise to a suspension of 5.7 g of 17α-chloroethynyl17α-hydroxy-4-androsten-3-one in 50 ml of acetic anhydride. After 5 minutes, the reaction mixture is introduced into methanol-containing ice water, the thus-precipitated product is suctioned off, dissolved in ethyl acetate, washed with water, and dried over sodium sulfate, yielding 5.1 g of 17α-chloroethynyl-17β-nitrooxy-4-androsten-3-one; mp 140° C. (decomposition).

(b) 4.0 g of 17α-chloroethynyl-17β-nitrooxy-4-androsten-3-one is dissolved in 10 ml of 1-methyl-2pyrrolidone. At 0° C., 46 ml of concentrated formic acid and 200 mg of silver nitrate are added to the mixture and the latter is agitated at room temperature. After 8 hours, the mixture is stirred into ice water. The thus-precipitated product is suctioned off, dissolved in ethyl acetate, washed with water, and dried over sodium sulfate, thus obtaining 3.2 g of 21-chloro-17-formyloxy-4-pregnene-3,20-dione; mp 204.9° C.

EXAMPLE 2

At room temperature, 1.6 g of 21-chloro-17- formyloxy-4-pregnene-3,20-dione is stirred in a mixture of 60 ml of methanol and 9 ml of water with 500 mg of potassium bicarbonate After one hour, the reaction mixture is stirred into ice water. The thus-precipitated product is suctioned off, washed with water, and dried over sodium sulfate, yielding 1.3 g of 21-chloro-17 TM hydroxy-4-pregnene-3,20-dione; mp 239.4° C.

EXAMPLE 3

1.0 g of 21-chloro-17-hydroxy-4-pregnene-3,20-dione in 20 ml of dimethylformamide is agitated at 80° C. with 1.0 g of potassium acetate. After 30 minutes, the reaction mixture is introduced into ice water, the precipitated product is suctioned off, dissolved in ethyl acetate, and dried over sodium sulfate, thus obtaining 940 mg of 21-acetoxy-17-hydroxy-4-pregnene-3,20-dione; mp 236.5° C.

EXAMPLE 4

(a) 11.5 g of 4,9(11)-androstadiene-3,17-dione [U.S. Pat. No. 3,441,559 (1969)]in 200 ml of dioxane is reacted with 20 ml of orthoformic acid trimethyl ester and 100 mg of p-toluenesulfonic acid. After 48 hours, 5 ml of pyridine is added to the solution, the latter is concentrated under vacuum, the residue taken up in ethyl acetate, washed with water, and dried over sodium sulfate. After chromatography of the crude product with a hexane-ethyl acetate gradient on silica gel containing 2% triethylamine, 9.2 g of 3-methoxy-3,5,9(11)-androstatrien-17-one is isolated; mp 153.4° C.

(b) At 0° C., 80 ml of a 1.5-molar methyllithium solution (in ether) is added dropwise to 6 ml of 1,2-dichloroethylene in 100 ml of absolute ether. After 30 minutes, 6.3 g of 3-methoxy-3,5,9(11)-androstatrien-17-one in 150 ml of absolute tetrahydrofuran is gradually added thereto. The reaction mixture is diluted with ether after 15 minutes and gently combined with 50 ml of saturated ammonium chloride solution. The organic phase is washed neutral with 2N hydrochloric acid and water, dried over sodium sulfate, and concentrated under vacuum. The resultant crude product is combined, in 30 ml of acetone, with 0.3 ml of 70% strength perchloric acid at room temperature. After 30 minutes, the reaction mixture is introduced into ice water; the precipitated product is suctioned off, dissolved in ethyl acetate, washed with water, and dried over sodium sulfate. Chromatography of the crude product on silica gel with a hexane-ethyl acetate gradient yields 6.0 g of 17α-chloroethynyl-17β-hydroxy-4,9(11)-androstadien-3-one; mp 157.1° C.

(c) Analogously to Example 1(a), 5.7 g of 17α- chloroethynyl-17ß-hydroxy-4,9(11)-androstadien-3-one is reacted with fuming nitric acid in acetic anhydride. After chromatography of the crude product on silica gel with a hexane-ethyl acetate gradient, 4.8 g of 17α-chloroethynyl17β-nitrooxy-4,9(11)-androstadien-3-one is obtained as a foam.

(d) 4.5 g of 17α-chloroethynyl-17β-nitrooxy4,9(11)-androstadien-3-one is reacted analogously to Example 1(b), thus obtaining 3.8 g of 21-chloro-17-formyloxy4,9(11)-pregnadiene-3,20-dione; mp 202.7° C.

EXAMPLE 4A

Analogously to Example 2, 2.5 g of 21 chloro-17-formyloxy-4,9(11)-pregnadiene-3,20-dione is reacted, yielding 2.2 g of 21-chloro-17-hydroxy-4,9(11)-pregnadiene-3,20dione; mp 236.9° C.

EXAMPLE 5

1.5 g of 21-chloro 17-hydroxy-4,9(11)-pregnadiene-3,20-dione is reacted in analogy to Example 3, thus producing 1.4 g of 21-acetoxy-17-hydroxy-4,9(11)-pregnadiene-3,20dione; mp 234.3° C.

EXAMPLE 6

(a) At room temperature, 1.5 g of 21-acetoxy-17-hydroxy-4,9(11)-pregnadiene-3,20-dione in 40 ml is agitated for 2 hours at room temperature with 15 ml of methanol 0.2N methanolic potassium hydroxide solution. The reaction mixture is introduced into ice water. The precipitated product is suctioned off, dissolved in methylene chloride, washed with water, and dried over sodium sulfate, thus obtaining 1.2 g of 17,21-dihydroxy-4,9(11) pregnadiene3,20-dione; mp 248.2° C.

(b) At 110° C., 20.0 g of 17α-chloroethynyl-17β-hydroxy-4-androsten-3-one in 1 1 of dioxane is stirred with 20.0 g of 2,3-dichloro-5,6-dicyano-p-benzoquinone. After 20 hours, the mixture is diluted with methylene chloride, washed with water and sodium bicarbonate solution, and dried over sodium sulfate. The crude product is chromatographed on silica gel with a hexane-ethyl acetate gradient. Yield: 14.7 g of 17α-chloroethynyl-17β-hydroxy-1,4-androstandien-3-one; mp 125.2° C.

(c) Analogously to Example 1(a), 8.0 g of 17α-chloroethynyl-17β-hydroxy-1,4-androstadien-3-one is reacted with fuming nitric acid, thus isolating 6.8 g of 17α-chloroethynyl-17β-nitrooxy-1,4-androstadien-3-one., Foam.

(d) 2.6 g of 17α-chloroethynyl-17β-nitrooxy-1,4-androstadien-3-one is reacted analogously to Example 1(b), thus obtaining 1.8 g of 21-chloro-17-formyloxy-1,4-pregnadiene-3,20-dione.

EXAMPLE 7

1 2 g of 21-chloro-17-formyloxy-1,4-pregnadiene3,20-dione is reacted analogously to Example 2, yielding 960 mg of 21-chloro-17-hydroxy-1,4-pregnadiene-3,20-dione.

EXAMPLE 8

Analogously to Example 3, 820 mg of 21-chloro-17-hydroxy-1,4-pregnadiene-3,20-dione is reacted to 21-acetoxy17-hydroxy-1,4-pregnadiene-3,20-dione. Yield: 710 mg; mp 215.8° C.

EXAMPLE 9

(a) 16.0 g of 17α-chloroethynyl-17β-hydroxy-4,9(11)-pregnadien-3 one is reacted analogously to Example 6(b) with 2,3-dichloro-5,6-dicyano-p-benzoquinone in dioxane, thus obtaining 9.8 g of 17α-chloroethynyl-17β-hydroxy-1,4,9(11)-androstatrien-3-one.

(b) Analogously to Example 1(a), 8.6 g of 17α-chloroethynyl-17β-hydroxy-1,4,9(11)-androstatrien-3one is reacted with fuming nitric acid, yielding 7.8 g of 17α-chloroethynyl-17β-nitrooxy-1,4,9(11)-androstatrien-3-one.

(c) 6.5 g of 17a-chloroethynyl-17β-nitrooxy-1,4,9(11)-androstatrien-3-one is reacted analogously to Example 1(b), thus obtaining 4.9 g of 21-chloro-17-formyloxy-1,4,9(11)-pregnatriene-3,20-dione.

EXAMPLE 10

Analogously to Example 2, 3.2 g of 21-chloro-17-formyloxy-1,4,9(11)-pregnatriene-3,20-dione is reacted to 21-chloro-17-hydroxy-1,4,9(11)-pregnatriene-3,20-dione. Yield: 2.9 g; mp 190.5° C.

EXAMPLE 11

1.2 g of 21-chloro-17-hydroxy-1,4,9(11)-pregnatriene-3,20-dione is reacted analogously to Example 3, thus obtaining 980 mg of 21-acetoxy-17-hydroxy-1,4,9(11) pregnatriene-3,20dione.

EXAMPLE 12

(a) Analogously to Example 4(a), 7.5 g of 6α-methyl-4,9(11)-androstadiene-3,17-dione is reacted to 3-methoxy-6-methyl-3,5,9(11)-androstatrien-17-one. Yield: 6.1 g.

(b) Analogously to Example 4(b), 5.5 g of 3-methoxy-6-methyl-3,5,9(11)-androstatrien-17-one yields 5.1 g of 17α-chloroethynyl-17β-hydroxy-6α-methyl-4,9(11)-androstadien-3-one.

(c) Analogously to Example 1(a), 4.5 g of 17α-chloroethynyl-17β-hydroxy-6α-methyl-4,9(11)-androstadien-3-one is reacted to 17α-chloroethynyl-17β-nitrooxy-6α-methyl-4,9(11)-androstadien-3-one. Yield: 3.8 g.

(d) Analogously to Example 1(b), 2.9 g of 17α-chloroethynyl-17α-17β-nitrooxy-6α-methyl-4,9(11)-androstadien-3-one is reacted to 21-chloro-17α-chloroethynyl-17β-nitrooxy-6α-methyl4,9(11)-pregnadiene-3,20-dione. Yield: 2.1 g.

EXAMPLE 13

Analogously to Example 2, 1.6 g of 21 TM chloro-17-formyloxy-6a-methyl-4,9(11)-pregnadiene-3,20-dione is reacted to 21-chloro-17-hydroxy-6α-methyl-4,9(11)-pregnadiene-3,20dione Yield: 1.3 g.

EXAMPLE 14

According to Example 3, 1.1 g of 21-chloro-17-hydroxy-6α-methyl-4,9(11)-pregnadiene-3,20-dione yields 870 mg of 21-acetoxy-17-hydroxy-6α-methyl-4,9(11)-pregnadiene3,20-dione.

EXAMPLE 15

(a) 12.5 g of 3β-hydroxy-D-homo-5-androsten-17a-one is reacted with lithium chloroacetylide analogously to Example 4(b). After chromatography of the crude product on silica gel with a hexane-acetone gradient, 8.9 g of 17aα-chloroethynyl-D-homo -homo-5 androstene-3β,17aβ-diol is obtained.

(b) About 5 ml of solvent is distilled off from a solution of 10.0 g of 17aα-chloroethynyl-D-homo-5-androstene-3β,17aβ-diol in 300 ml of toluene and 50 ml of cyclohexanone. While continuing removal of solvent by distillation, 4.0 g of aluminum triisopropylate in 30 ml of toluene is added dropwise After 1.5hours, 50.0 g of potassium-sodium tartrate in 70 ml of water is gradually added to the mixture and the latter stirred for 30 minutes under reflux. After cooling the solution, it is diluted with ethyl acetate, the organic phase is repeatedly washed with water, and dried over sodium sulfate. Chromatography of the crude product on silica gel with a hexane-acetone gradient yields 8.4 g of 17aα-chloroethynyl-17aβ-hydroxy-D-homo-4-androsten-3-one. homo-4-androsten-3-one.

(c) Analogously to Example 1(a), 8.3 g of 17aα-chloroethynyl-17aαchloroethynyl-17aβ-hydroxy-D-homo-4-androsten-3-one is reacted to 17aα-chloroethynyl-17a8-nitrooxy-D-homo-4-androsten-3-one. Yield: 6.7 g.

(d) 6.3 g of 17aα-chloroethynyl-17aβ-nitrooxy -D-homo-4-androsten-3-one is reacted analogously to Example 1(b), thus isolating 4.3 g of 21-chloro-17aα-formyloxy-D -homo-4-pregnene-3,20-dione.

EXAMPLE 16

Analogously to Example 2, 3.8 g of 21-chloro-17aα-formyloxy-D-homo-4-pregnene-3,20-dione is reacted to 21-chloro-17aα-hydroxy-D-homo-4-pregnene-3,20-dione. Yield: 3.1 g.

EXAMPLE 17

2.4 g of 21-chloro-17aα-hydroxy-D-homo-4-pregnene-3,20-dione is reacted analogously to Example 3 to 21-acetoxy-17aα-hydroxy-D-homo-4-pregnene-3,20-dione. Yield: 2.1 g.

EXAMPLE 18

(a) At 0° C, 3.4 ml of trifluoroacetic anhydride is added dropwise to 5.0 g of 17α-chloroethynyl-17β-hydroxy4-androsten-3-one in 25 ml of pyridine. After 30 minutes, the reaction mixture is introduced into hydrochloric ice/water. The precipitated product is suctioned off, washed with water, and dried. After chromatography of the crude product on silica gel with hexane-ethyl acetate, 4.1 g of 17α-chloro -ethynyl-17β-trifluoroacetoxy-4-androsten-3-one is obtained; mp 139° C.

(b) At 60° C., 3.5 g of 17α-chloroethynyl-17β-trifluoroacetoxy-4-androsten-3-one is agitated in 30 ml of concentrated formic acid and 6 ml of 1-methyl-2-pyrrolidone with 300 mg of silver nitrate. After 6 hours, the reaction mixture is introduced into ice water. The precipitated product is suctioned off, washed with water, and dried. Chromatography of the crude product on silica gel with hexane-ethyl acetate yields 1.3 g of 21-chloro-17-formyloxy-4-pregnene-3,20-dione; mp 201.5° C.

EXAMPLE 19

(a) At 0° C., 3.5 ml of trichloroacetic anhydride is added dropwise to 5.0 g of 17α-chloroethynyl-17β-hydroxy-4-androsten-3-one in 30 ml of pyridine. After 15 minutes, the reaction mixture is introduced into ice-/water that contains sulfuric acid. The precipitated product is taken up in ethyl acetate. After chromatography of the crude product on silica gel with hexane-ethyl acetate, 4.8 g of 17α-chloroethynyl-17β-trichloroacetoxy-4-androsten-3-one is obtained; mp 173° C.(decomposition).

(b) 1.4 g of 17a-chloroethynyl-17β-trichloro-acetoxy-4-androsten-3-one is reacted—as described in Example 18(b)—in concentrated formic acid and 1-methyl2-pyrrolidone with silver nitrate. Chromatography of the crude product on silica gel with hexane-ethyl acetate yields 630 mg of 21-chloro-17-formyloxy-4-pregnene-3,20dione; mp 202.5° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a pregnane derivative of the formula

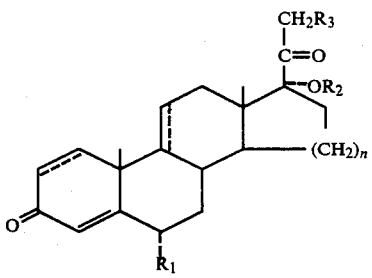

wherein
· · · · · in each case is a single or double bond,
n is 1 or 2,
$R_2$ is hydrogen or formyl, and
$R_3$ is chlorine, hydroxy or alkanoyloxy of up to 6 carbon atoms,
comprising esterifying an androstane derivative of the formula

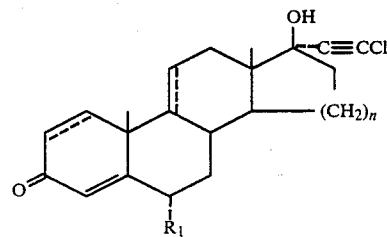

wherein · · · ·, n and $R_1$ are as defined above, with nitric acid, trifluoroacetic acid, trichloroacetic acid, or a reactive derivative thereof, thereby forming the corresponding ester of the formula

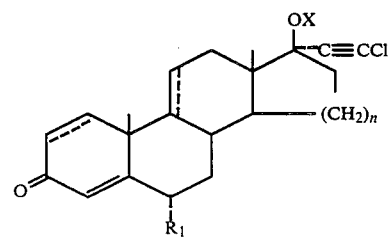

wherein · · ·, n and R as defined above and
X is nitro, trifluoroacetyl, or trichloroacetyl,
reacting the latter ester in the presence of a catalytically effective amount of silver(I), with formic acid to form the pregnane of the formula

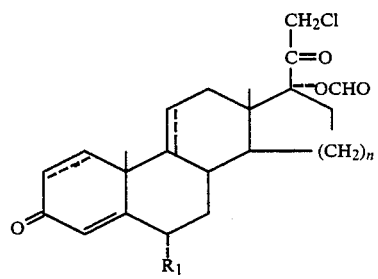

wherein · · · ·, n and $R_1$ are as defined above, and, optionally, (a) saponifying the thus produced 17-formyl ester, (b) exchanging the 21-chlorine atom against an alkanoyloxy group, or (c) exchanging the 21-chlorine atom against the alkanoyloxy group and saponifying the latter.

2. A process of claim 1 wherein the esterifying agent is nitric acid or a reactive derivative thereof.

3. A process of claim 1 wherein the esterifying reagent is acetyl nitrate.

4. A process of claim 1 wherein the esterifying reagent is trichloroacetic acid or a reactive derivative thereof.

5. A process of claim 1 wherein the esterifying reagent is trifluoroacetic acid or a reactive derivative thereof.

6. A process of claim 1 wherein the silver(I) cations are introduced into the reaction by addition of a readily dissociated salt of silver(I).

7. A process of claim 1 wherein 0.01–0.5 mole of a dissociating silver(I) salt, based on the amount of steroid, is used.

8. A process of claim 1 wherein the silver(I) is provided in the form of silver(I) nitrate, silver(I) acetate, silver(I) fluoride, or silver(I) sulfate.

9. A process of claim 1 wherein the reaction of said ester is conducted in a mixture of formic acid and a dipolar aprotic or alkaline solvent.

10. A process for preparing a pregnane derivative of the

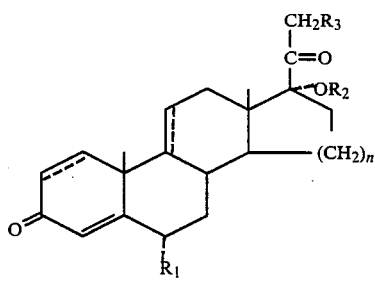

wherein

・・・・ in each case is a single or double bond, n is 1 or 2, $R_1$ is hydrogen or methyl, $R_2$ is hydrogen or formyl, and $R_3$ is chlorine, hydroxy or alkanoyloxy of up to 6 carbon atoms, comprising reacting an ester of the formula

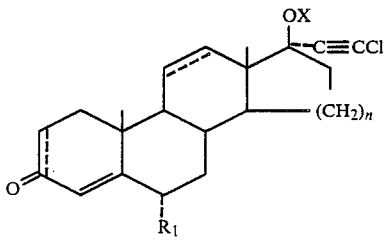

wherein

・・・・, n and $R_1$ as defined above and X is nitro, trifluoroacetyl, or trichloroacetyl in the presence of a catalytically effective amount of silver(I), with formic acid to form the pregnane of the formula

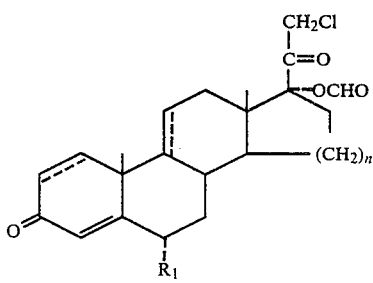

wherein ・・・・, n and $R_1$ are as defined above, and, optionally, (a) saponifying the thus produced 17-formyl ester, (b) exchanging the 21-chlorine atom against an alkanoyloxy group, or (c) exchanging the 21-chlorine atom against the alkanoyloxy group and saponifying the latter.

* * * * *